(12) United States Patent
Lee et al.

(10) Patent No.: US 7,964,078 B2
(45) Date of Patent: Jun. 21, 2011

(54) MICROFLUIDIC DEVICE FOR CELL AND PARTICLE SEPARATION

(75) Inventors: Abraham P. Lee, Irvine, CA (US); Lisen Wang, Irvine, CA (US); Lisa Flanagan Monuki, Irvine, CA (US); Edwin S. Monuki, Irvine, CA (US); Svyatoslav A. Marchenko, North Hollywood, CA (US)

(73) Assignee: The Regents of the University of California, Oakland, CA (US)

( * ) Notice: Subject to any disclaimer, the term of this patent is extended or adjusted under 35 U.S.C. 154(b) by 1175 days.

(21) Appl. No.: 11/670,945

(22) Filed: Feb. 2, 2007

(65) Prior Publication Data

US 2007/0125941 A1 Jun. 7, 2007

Related U.S. Application Data

(63) Continuation-in-part of application No. 11/557,060, filed on Nov. 6, 2006.

(60) Provisional application No. 60/743,220, filed on Feb. 2, 2006.

(51) Int. Cl.
*B03C 5/02* (2006.01)
(52) U.S. Cl. ........................ 204/643; 204/547
(58) Field of Classification Search .............. 204/547, 204/643
See application file for complete search history.

(56) References Cited

U.S. PATENT DOCUMENTS 6,146,103 A * 11/2000 Lee et al. ........................ 417/50
6,936,811 B2 8/2005 Kibar
2002/0088712 A1 * 7/2002 Miles ............................ 204/547
2004/0091392 A1 * 5/2004 McBride et al. ................ 422/57
2005/0072677 A1 * 4/2005 Gascoyne et al. ............ 204/547

OTHER PUBLICATIONS

Yang, Jun, et al., "Cell Separation on Microfabricated Electrodes Using Dielectrophoretic/Gravitational Field-Flow Fractionation", Anal. Chem. vol. 71, No. 5, Mar. 1, 1999, pp. 911-918.
Fu, Anne Y., et al., "A Microfabricated Fluorescence-Activated Cell Sorter", Nature Biotechnology, vol. 17, Nov. 1999, pp. 1109-1111.
Heida, Tjitske, et al., "Dielectrophoretic Trapping of Dissociated Fetal Cortical Rat Neurons", IEEE Transactions on Biomedical Engineering, vol. 48, No. 8, Aug. 2001, pp. 921-930.

(Continued)

*Primary Examiner* — Ula C Ruddock
*Assistant Examiner* — J. Christopher Ball
(74) *Attorney, Agent, or Firm* — Vista IP Law Group LLP (57) ABSTRACT

A microfluidic separation device includes a microchannel formed in a substrate and being defined at least by a bottom surface, a first side wall, and second side wall. Fluid containing particles or cells is flowed through the microchannel from an upstream end to a downstream end. The downstream end terminates in a plurality of branch channels. A plurality of vertically-oriented electrodes are disposed on the first wall and on the second wall opposite to the first wall. A voltage source is connected to the plurality of opposing electrodes to drive the electrodes. The opposing, vertically-oriented electrodes may be used to focus a heterogeneous population of particles or cells for subsequent downstream separation via additional electrodes placed on one of the side walls. Alternatively, the opposing, vertically-oriented electrodes may be used to spatially separate a heterogeneous population of particles or cells for later collection in one or more of the branch channels.

15 Claims, 7 Drawing Sheets

OTHER PUBLICATIONS

Lemoff, A.V., et al., "An AC Magnetohydrodynamic Microfluidic Switch", U.S. Department of Energy, Lawrence Livermore National Laboratory, UCRL-JC-137192, MicroTAS 2000, The Netherlands, May 14-18, 2000 [6pp].

Taff, B.M., et al., "A Scalable Row/Column-Addressable Dielectrophoretic Cell-Trapping Array", Massachusetts Institute of Technology, USA, 9$^{th}$ International Conference on Miniaturized Systems for Chemistry and Life Sciences, Oct. 9-13, 2005, Boston, Massachusetts, USA, pp. 865-867.

* cited by examiner

MICROFLUIDIC DEVICE FOR CELL AND PARTICLE SEPARATION

REFERENCE TO RELATED APPLICATIONS

This Application claims priority to U.S. Provisional Patent Application No. 60/743,220 filed on Feb. 2, 2006. The '220 application is incorporated by reference as if set forth fully herein. This Application is also a continuation-in-part of U.S. patent application Ser. No. 11/557,060 filed on Nov. 6, 2006, which itself claims priority to U.S. Provisional Patent Application No. 60/734,544 filed on Nov. 7, 2005. The '060 and '544 applications are incorporated by reference as if set forth fully herein.

FIELD OF THE INVENTION

The field of the invention generally relates to devices used to separate and sort particles or cells. More particularly, the invention relates to microfluidic-based devices that separate and/or sort biological materials (e.g., cells or cellular components) or particles.

BACKGROUND OF THE INVENTION

Microfluidic-based systems are becoming widely used in biological and chemical analysis applications. Traditionally, flow cytometry has been used to separate or sort a cell or particle of interest from a heterogeneous population. For example, in conventional flow cytometry, a mixture or cells or particles is hydrodynamically focused using a sheath fluid. The cells or particles, which may be labeled with a fluorescent label or the like, is then interrogated using, for example, a laser or other optical apparatus to identify particular cells or particles of interest within the stream. The cells or particles of interest can then be deflected downstream of the interrogation region into an appropriate collection chamber or the like by using high-voltage electrical plates. For example, the cell or particle contained within the droplet of carrier fluid may be positively or negatively charged which can then be attracted (or repulsed) by the charged electrical plates. This causes movement of the droplets into the proper collection chamber.

More recently, various microfluidic-based sorting schemes have been envisioned to sort cells. For example, Fu et al. discloses a microfabricated fluorescence-activated cell sorter that uses electrokinetic flow to sort bacteria and particles. See Fu et al., A microfabricated fluorescence-activated cell sorter, Nature Biotechnology, 17, 1109-111 (1999). U.S. Pat. No. 6,936,811 discloses a microfluidic sorting device that uses a moving optical gradient to sort particles or cells based on their dielectric properties. Still others have disclosed the use of microfabricated electrodes to separate cells using dielectrophoretic/gravitational field-flow fractionation (DEP/G-FFF). See Yang et al., Cell separation on microfabricated electrodes using dielectrophoretic/gravitational field-flow fractionation, Anal. Chem., 71(5):911-918 (1999). In the DEP/G-FFF method, cells are "levitated" to different heights according to the balance of the DEP and gravitational forces. In still another strategy, cell trapping arrays have been proposed that "trap" cells at dielectrophoretic (DEP) traps. See Heida et al., Dielectrophoretic trapping of dissociated fetal cortical rat neurons, Biomedical Engineering, IEEE Transactions of Biomedical Engineering, Vol. 48, No. 8, August 2001; Taff et al., A Scalable Row/Column-Addressable Dielectrophoretic Cell-Trapping Array, $9^{th}$ Intl., Conf. on Miniaturized Sys. For Chemistry and Life Sciences, October 2005.

Unfortunately, many of the proposed sorting schemes set forth above have significant limitations. For instance, DEP/G-FFF based devices which rely on the balance between the DEP force and the gravitation force is heavily dependent on the velocity control of the flow since those cells or particles in the middle of the channel are flushed out first because of the parabolic flow profile created within the channel. Also, this method suffers from poor discrimination since the particles/cells located at the sides of the microchannel can be eluted along with the "faster" fraction located within the central region of the channel. In addition, devices using DEP/G-FFF or trapping sort cells or particles temporally (e.g., a time-based approach) making throughput low. Because of this, complicated valves and pumps are needed if this type of separation approach were integrated with other sample preparation steps.

There thus is a need for a device and method that is capable of sorting particles and cells using a spatial approach. Namely, heterogeneous mixtures of cells and/or particles may be automatically directed to downstream channels, branches, or collection chambers without the need for ancillary pumps or valves that control flow patterns. In this regard, the sorting device may be integrated into a microfluidic-based total analysis system that includes other process steps like sample preparation. The device should also permit the sorting of heterogeneous mixtures of cells and/or particles without the need of any fluorescent labels or biomarkers.

SUMMARY

In one embodiment of the invention, a microfluidic separation device includes a microchannel formed in a substrate and being defined at least by a bottom surface, a first side wall, and second side wall. Fluid containing particles or cells is flowed through the microchannel from an upstream end to a downstream end. The downstream end terminates in a plurality of branch channels. A plurality of vertically-oriented electrodes are disposed on the first wall and on the second wall opposite to the first wall. A voltage source is connected to the plurality of opposing electrodes to drive the electrodes. The opposing, vertically-oriented electrodes may be used to focus a heterogeneous population of particles or cells for subsequent downstream separation via additional electrodes placed on one of the side walls. Alternatively, the opposing, vertically-oriented electrodes may be used to spatially separate a heterogeneous population of particles or cells for later collection in one or more of the branch channels.

In another embodiment of the invention, a microfluidic separation device includes a first microchannel formed in a substrate, the first microchannel being defined by a bottom surface, a first wall, and a second wall. The first microchannel includes an upstream end and a downstream end. A focusing region is disposed in the first microchannel and includes a plurality of electrodes disposed on the first wall and another plurality of electrodes disposed on the second wall opposite the plurality of electrodes disposed on the first wall. A voltage source is connected to the plurality of electrodes on the first wall and the second wall. A separation region is disposed in the first microchannel at a location downstream of the focusing region, the separation region comprising a plurality of electrodes disposed on one of the first and second walls of the first microchannel. The device includes a plurality of branch microchannels coupled to a downstream end of the first microchannel.

In another aspect of the invention, a method of sorting particles or cells using a microfluidic device includes providing a microfluidic channel having a bottom surface and two opposing side walls, the microfluidic channel having a focusing region comprised of a plurality of electrodes disposed on opposing side walls of the microchannel. The microfluidic channel further includes a separation region located downstream of the focusing region and includes a plurality of electrodes on one of the opposing side walls, the microchannel further includes a plurality of branch channels located downstream of the separation region. A heterogeneous population of particles or cells is flowed within the microfluidic channel. The plurality of electrodes in the focusing region are driven to focus or align the heterogeneous population of particles or cells. The plurality of electrodes in the separation region are then driven so as to spatially separate the heterogeneous population of particles or cells. The spatially separated heterogeneous population of particles or cells is then flowed into the plurality of branch channels based, at least in part, on the spatial separation.

In another aspect of the invention, a method of sorting particles or cells using a microfluidic device includes providing a microfluidic channel having a bottom surface and two opposing side walls, the microfluidic channel including a plurality of electrodes disposed on opposing side walls of the microchannel. A plurality of branch channels are connected to main microfluidic channel at a downstream location. A heterogeneous population of particles or cells is flowed within the microfluidic channel. The plurality of electrodes are driven so as to spatially separate the heterogeneous population of particles or cells within the microchannel. The now separated population of particles or cells are then sorted by flow into the plurality of branch channels based, at least in part, on the spatial separation.

In another embodiment of the invention, a method of sorting particles or cells using a microfluidic device includes providing a microfluidic channel having a bottom surface and two opposing side walls, the microfluidic channel including a plurality of DEP electrodes disposed on a side wall of the microchannel. The microchannel further includes a plurality of branch channels located downstream of the plurality of DEP electrodes. A heterogeneous population of particles or cells is flowed within the microfluidic channel. The plurality of DEP electrodes are driven so as to trap a portion of the heterogeneous population of particles or cells at a location within the microchannel that is adjacent to the DEP electrodes. The un-trapped heterogeneous population of particles or cells is then flowed within a first branch channel. The portion of the heterogeneous population of particles or cells that is trapped at the DEP electrodes is then released into the flowing fluid by turning off or de-energizing the DEP electrodes. The released portion of particles or cells is then flowed into a second branch channel.

DETAILED DESCRIPTION OF THE INVENTION

Figure 1:
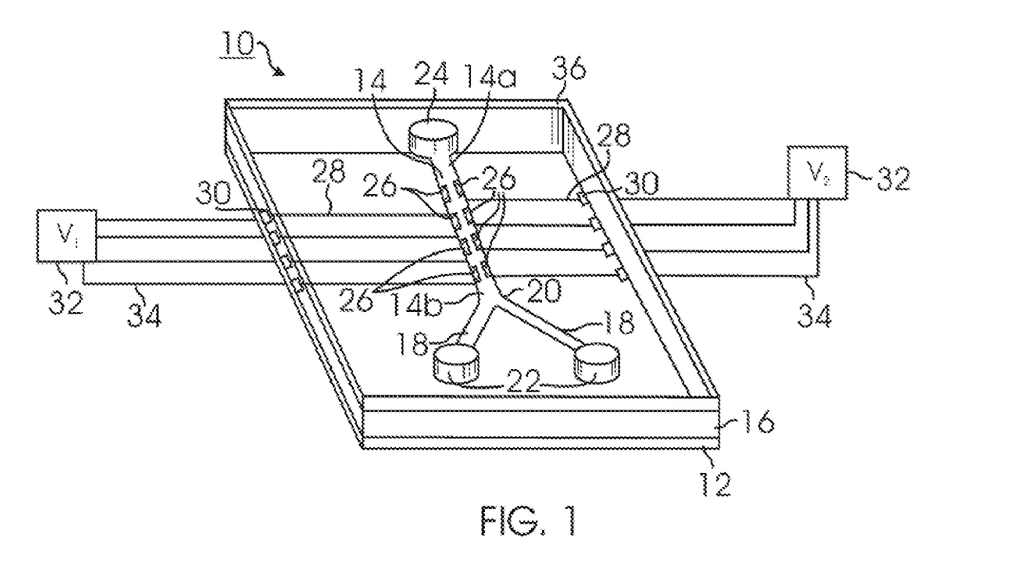
FIG. 1 illustrates a perspective view of an embodiment of a microfluidic device having a channel with vertical microelectrodes contained therein.

FIG. 1 illustrates a microfluidic device 10 according to one embodiment of the invention. The microfluidic device 10 includes a substrate 12 onto which the device 10 is formed. The substrate 12 may include a relatively inert material such as silicon, glass, polycarbonate, or a plastic-based material. The substrate 12 should be amenable to depositing the electrodes and electrical lines or traces used to drive the electrodes (discussed in more detail below).

A main or common microchannel 14 is formed in a polymer-based material 16 that overlays the substrate 12. The polymer-based material 16 may include a photoresist such as, for instance, SU-8. As seen in FIG. 1, the microchannel 14 has a length that includes an upstream region 14a, and a downstream region 14b. The terms upstream and downstream are indicative of the direction of flow of fluid and particles or cells within the microchannel 14 during operation. During operation, fluid flow (and hence flow of particles or cells) goes from the upstream region 14a toward the downstream region 14b.

As seen in FIG. 1, the main or common microchannel 14 includes a plurality of downstream branch channels 18 that are joined to the common microchannel 14 at the downstream region 14b at a junction 20. In the embodiment of FIG. 1, two branch channels 18 are illustrated but the device 10 may include any number of branch channels 18 greater than two (2). Also, as seen in FIG. 1, the branch channels 18 terminate in two collection chambers 22 which, in certain embodiments, may be used to collect the sorted particles or cells. It should be understood, however, that the branch channels 18 may be coupled to other microfluidic channels, mixing regions, reaction chambers, and the like, which can be used for various post-sorting operations. In this regard, the device 10 is particularly well suited for integrated lab-on-a-chip devices or systems which integrate numerous processes into a single device.

FIG. 1 also illustrates an inlet chamber 24 that is coupled to the upstream region 14a of the main microfluidic channel 14. A heterogeneous population of cells or particles may be loaded into the device 10 via the inlet chamber 24. The population of cells or particles would, of course, be loaded or carried by a carrier fluid. The carrier fluid is typically a biologically-compatible fluid such as, for example, a water-based isotonic solution. In the case of particles, however, it may be possible to use one or more organic-based carrier fluids. The inlet chamber 24 may, alternatively, be coupled to fluid source via tubing or conduit to a pump or the like that loads and transports cells or particles into the device 10. In still another alternative, various microfluidic channels, chambers, or the like (not shown) may be coupled to the upstream portion 14a of the main channel 14. For example, various sample preparation processes may take place upstream of the main channel 14 in one or more microfluidic features that are contained on an integrated device 10.

Figure 2A:
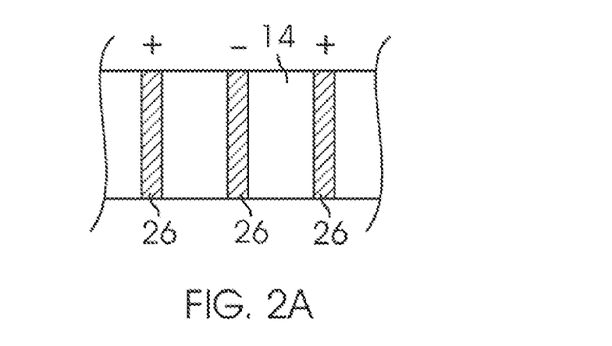
FIG. 2A illustrates a partial side view of the side wall of a microchannel having a plurality of vertically oriented electrodes.
Figure 2B:
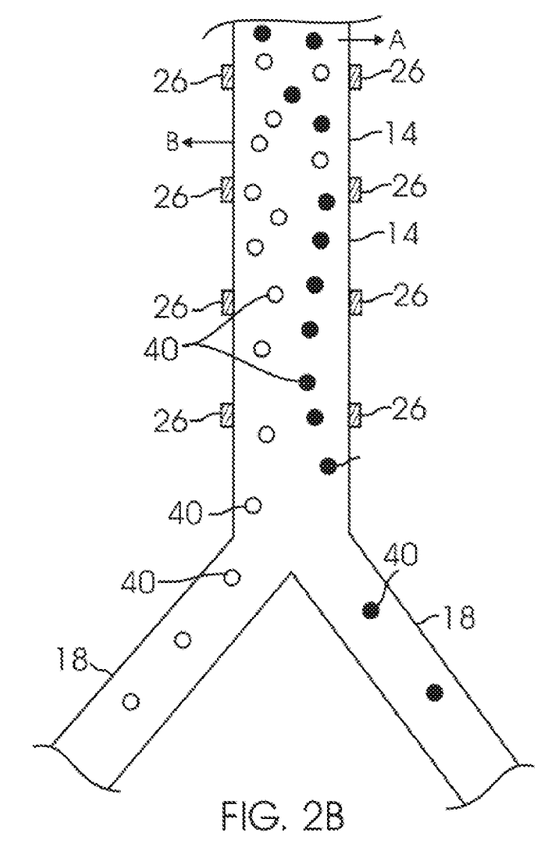
FIG. 2B illustrates a top down view of a microfluidic device having a common channel along with two downstream branch channels. Opposing arrays of electrodes are positioned on the side walls of the microchannel.

Still referring to FIG. 1, a plurality of opposing, vertically-oriented electrodes 26 are disposed on opposite sides of the side walls of the microchannel 14. The vertically-oriented electrodes 26 may be formed from an electrically-conductive material such as, for instance, platinum, gold, carbon, or other biologically inert material. As seen in FIG. 1, the electrodes 26 generally are formed in pairs with adjacent electrodes 26 being of opposite polarity (as seen in FIG. 2B). FIG. 1 illustrates two pairs on either side of the microchannel 14 (i.e., a total of four electrodes 26 on each side) but there may be more depending on the particular application.

Each electrode 26 is coupled to respective electrical traces or lines 28. The electrical traces or lines 28 may be formed from an electrically-conductive material such as, for instance, gold, platinum or the like. As seen in FIG. 1, each electrical trace or line 28 may terminate in an electrical contact or pad 30. The electrical contact 30 for each electrode 26 may then be connected to a voltage source 32 via leads or wires 34. As seen in FIG. 1, separate voltage sources 32 ($V_1$ and $V_2$) may be connected to the electrodes 26 on the opposing side walls of the microchannel 14. In the case of dielectrophoresis (DEP) electrodes 26, the voltage source 32 preferably has the ability to adjust the applied frequency (AC mode) as well as the voltage (e.g., amplitude). For example, a dual channel function generator like the Tektronix AFG320 may be used to input signals to the opposing electrode arrays of electrodes 26 on either side of the microchannel 14. The particulars of the forces generated by the electrodes 26 is discussed more detail herein.

The nature of the electrodes 26 along the opposing side walls of the microchannel 14 may vary. For example, in one embodiment (e.g., FIG. 4) the opposing plurality of electrodes are all DEP electrodes. In particular, DEP electrodes induce forces on the cells or particles that is generally perpendicular to the direction of flow within the microchannel 14. The forces are a function of, among other things, the dielectric constant of the particle or cell. The forces may be attractive or repulsive. In another embodiment, the opposing plurality of electrodes 26 along the walls of the microchannel 14 may be magneto-hydrodynamic electrodes (MHD). MHD electrodes are typically driven by AC current although in some applications DC current may be applied. MHD electrodes typically operate by application of AC electrical current and a perpendicular sinusoidal AC magnetic field that pass through an electrolytic solution. This produces a Lorentz force, which in embodiments described herein, is generally perpendicular to the direction of fluid flow (i.e., from one side wall to the other).

Figure 3:
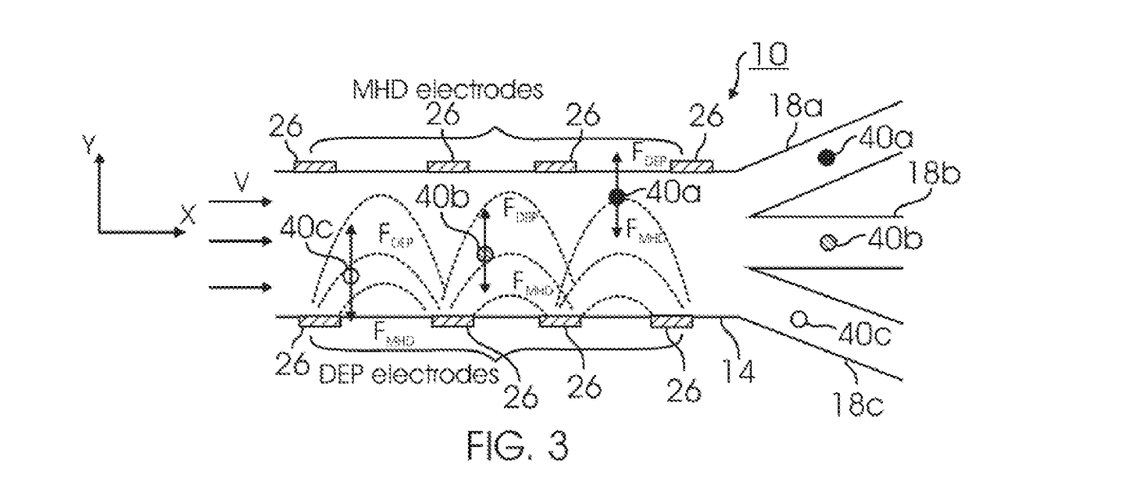
FIG. 3 illustrates an embodiment of a microfluidic device having MHD and DEP electrodes. Separation and sorting can be accomplished in three downstream branch channels.
Figure 7:
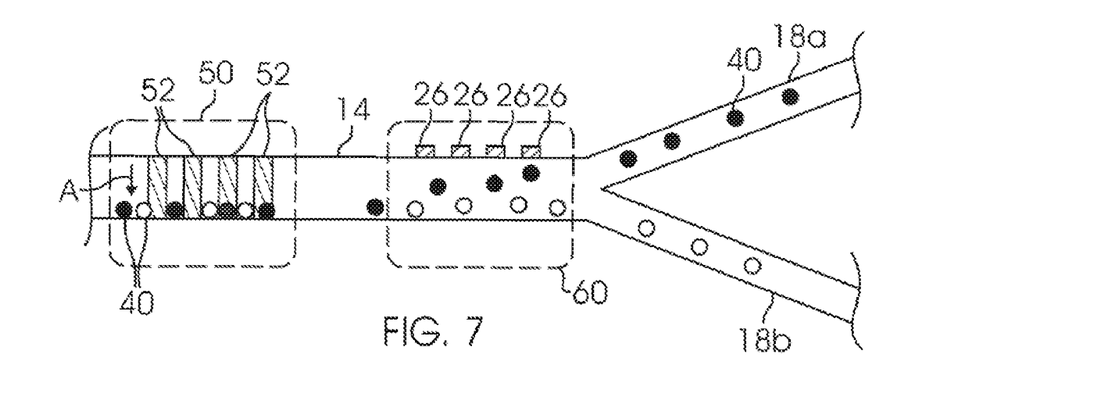
FIG. 7 illustrates another embodiment of a microfluidic device having an upstream focusing region and a downstream separation region.

In the embodiments described herein, MHD electrodes 26 may be oriented vertically along the walls of the microchannel 14, for example, as shown in FIG. 3. Alternatively, the MHD electrodes 26 may be oriented perpendicular to the direction of flow within the microchannel 14, as is shown in FIG. 7. MHD electrodes 26 produce a substantially uniform force on the carrier fluid that contains the particles or cells. MHD electrodes 26 are thus well suited for pumping applications as well as focusing or alignment procedures as discussed in more detail below.

The electrodes 26 may be arranged within the microchannel 14 in any number of configurations that are suitable for the particular application of interest. For example, the electrodes 26 may interdigitated on opposing side walls of the microchannel 14. The electrodes 26 may be symmetric or un-symmetric depending on the desired field effect (e.g., DEP or MHD field). The electrodes 16 may be smooth or have sharp edges. In addition, in some embodiments, such as that disclosed later in FIG. 7 may include MHD electrodes 26 arranged flat on the bottom surface of the microchannel 14. In addition, DEP electrodes 26 may be arranged in a flat or flush orientation with the side walls of the microchannel 14.

Still referring to FIG. 1, an optional cap or cover 36 is positioned over the polymer-based material 16 in which the microchannel 14 is formed. Preferably, the polymer-based material 16 is flexible so that a good seal can be formed between the cover 36 and the underlying material 16. Of course, it may be possible to use a rigid or semi-rigid material for the cap 36. For example, glass or plastic may be used to form the cap 36.

The microfluidic device 10 may formed using a combination of photolithographic, metal deposition, and electroplating techniques. For example, the substrate 12 may be coated with an adhesion layer of photoresist (SU-8) followed by deposition and patterning of thin metal layers for the electroplating of the vertically oriented electrodes 26. The electrodes 26 may be electroplated through a SU-8 mold layer which is then removed. The SU-8 channel layer 16 can be coated and patterned with alignment of the microchannel 14 and the electrodes 26. The alignment of the electrodes 26 and the side walls of the microchannel 14 ensures that the electrodes 26 can be exposed to the fluid contained within the microchannel 14. A flexible PDMS sheet coated with a thin layer of SU-8 may be used as the cap 36 to seal the microchannel 14. Further details on the process of forming vertically oriented electrodes 26 on the side walls of the microchannel 14 may be found in U.S. patent application Ser. No. 11/557,060 which is incorporated by reference as if set forth fully herein.

The opposing vertical electrodes 26 may be located along the full height or depth of the side walls forming the microchannel 14 so as to avoid any dead electrical field zones. This is illustrated in FIG. 2A, which shows three such electrodes 26 traversing the entire height of the microchannel 14. FIG. 2B illustrates a top-down view of a microchannel 14 with two branch channels 18. Also shown are a heterogeneous population of cells 40. The population illustrated in FIG. 2B has two types of cells (represented by solid circles and open circles). It should be understood that the cells 40 could also be particles and still work in accordance with the invention described herein.

In this embodiment, one type of cells 40 (i.e., solid circles) experience a force in the direction of arrow A while the other type of cell 40 (open circles) experience a force B in the direction of arrow B. In this embodiment, both sets of opposing electrodes 26 are DEP electrodes. As the heterogeneous population of cells 40 passes through the region of the microchannel 14 that contains the electrodes 26, the cells are spatially separated along the width of the microchannel 14. Specifically, the cells 40 represented by the solid circles move toward and ultimately into the branch channel 18 on the right while the cells represented by the open circles move toward and ultimately into the branch channel 18 on the left. It should be understood that the spatial separation of the cells 40 determines what branch channel 18 a particular cell 40 will go into.

FIG. 3 illustrates a top view of an embodiment of a device 10 that includes a microchannel 14 having a plurality of vertically oriented, MHD electrodes 26 positioned along one side of the wall of the microchannel 14. The other, opposing side wall of the microchannel 14 has a plurality of vertically oriented, DEP electrodes 26. Three types of cells 40a, 40b, 40c are shown being directed into three downstream branch channels 18a, 18b, 18c. Fluid flow is in the direction of the arrows V in FIG. 3. FIG. 3 illustrates the electrical field from the DEP electrodes 26. Also shown is the force balance diagram for the DEP force ($F_{DEP}$) and the MHD force ($F_{MHD}$). The MHD force is generally perpendicular to the direction of flow (V) within the microchannel 14 and tends to move the cells 40a, 40b, 40c toward the side of the microchannel 14 containing the DEP electrodes 26. The MHD force is typically a substantially uniform force as it generally acts upon the fluid carrying the cells 40a, 40b, 40c.

In contrast, the DEP force, while also being directed perpendicular to the direction of fluid flow (V), tends to move the cells 40a, 40b, 40c in the opposite direction, toward the side wall of the microchannel 14 having the MHD electrodes 26. The DEP force is non-uniform and affects the different types of cells 40a, 40b, 40c differently. For example, the cell 40a experiences a large DEP force, the pushes the cell 40a towards the top of the microchannel 14. Because of this, the cell 40a is transferred into the top branch channel 18a. The cell 40b experiences a medium DEP force and pushes the cell 40b generally in the middle of the microchannel 14 as seen in FIG. 3. The cell 40b then flows downstream and into the middle branch channel 18b. Finally, the cell 40c experiences a light DEP force. As a result, the cell 40c generally stays close to the lower region of the microchannel 14 and then flows into the lower branch channel 18c.

Figure 4:
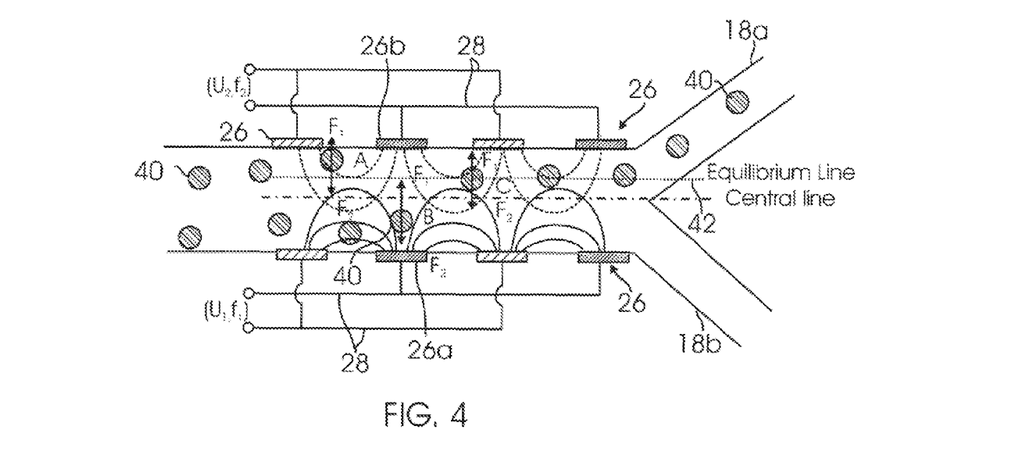
FIG. 4 illustrates a DEP-DEP microfluidic device that uses opposing pairs of DEP electrodes to focus or fine tune the equilibrium line of particles flowing through a microchannel.

FIG. 4 illustrates yet another embodiment wherein vertically oriented DEP electrodes 26 are positioned on both side walls of the microchannel 14. FIG. 4 further illustrates the electrical lines or traces 28 that connect the electrodes 26. As seen in FIG. 4, the electrodes 26 alternate in polarity along the length of the side wall of the microchannel 14 (e.g., arranged in an interdigitated manner). In the configuration of FIG. 4, the DEP force created by the DEP electrodes 26 on one side wall can be used to counteract and balance against the DEP force created by the DEP electrodes 26 on the opposing side wall of the microchannel 14.

FIG. 4 further illustrates the force balance of particles between the two sets of side wall electrode arrays. A signal ($U_1$, $f_1$) is applied to the bottom array of electrodes 26, generating an upwards negative DEP force $F_1$ on the particles. In FIG. 4, U represents a voltage while f represents an applied frequency. A second signal ($U_2$, $f_2$) is applied on the top electrodes 26 to generate a counter force $F_2$ to the force generated by the first (i.e., top) set of electrodes 26. By varying the magnitude and frequencies of the voltages, the forces ($F_1$, $F_2$) from these two sets of electrodes 26 can balance each other, and the cells 40 (or particles) can therefore be spatially positioned at an equilibrium point 42. The equilibrium point 42, in which the two opposing forces $F_1$, $F_2$ equal each other, is unique for a particular cell type 40 and can be used as a basis for downstream sorting as described herein. For example, a cancerous cell 40 may have an equilibrium point 42 at a spatial location nearer to the upper electrodes 26 while a non-cancerous or normal cell 26 may have an equilibrium point 42 at a spatial location nearer to the lower electrodes 26.

Still referring to FIG. 4, when a cell 40 is close to electrode 26a, like the one at point B, the DEP force $F_1$ from electrode 26a is larger than the DEP force $F_2$ from electrode 26b, the cell will be pushed upwards (because of the larger repulsive force from electrode 26a). With the movement away from the bottom electrode 26, the DEP force $F_1$ decreases and $F_2$ increases until it reaches an equilibrium position 42 where $F_1$ is equal to $F_2$ at point C. The line that passes through point C along the direction of the microchannel 14 is the equilibrium point 42 (or line) for the cells 40 at the applied driving frequency and amplitude. The two DEP forces ($F_1$, $F_2$) can be adjusted by changing the voltage U or the frequency f, so that the equilibrium line 42 can be tuned to any location along the width of the microchannel 14. For example, tuning can be used to displace the equilibrium line 42 above the centerline of the microchannel 14 as is shown in FIG. 4. In this configuration, the cells 40, which are moving in a continuously flowing carrier fluid, are moved to the upper branch channel 18a. Alternatively, the equilibrium line 42 may be tuned to fall bellow the centerline and thereby cause the cells 40 to pass into the lower branch channel 18b.

This embodiment is suited for forming devices 10 that acts as a microfluidic switch. Because of the effect of the coupled DEP forces, objects of interest such as cells 40 (or particles) can be positioned at any equilibrium position in the microchannel 14. The device 10 thus permits spatial tuning in the lateral direction within the microchannel 14. The embodiment is particularly well-suited for switching applications that having multiple outlets or branch channels 18. Only two electrical signal inputs are required to switch the cells 40 or particles to multiple channels. This type of design may be integrated together with other cell separation techniques such as field flow fractionation to switch multiple types of cells 40 at different times in a continuous manner. This design is also very compatible with other microfluidic sample preparation steps. Multiple types of objects (e.g., cells or particles) can be serially switched to different branch channels 18 and processed in parallel. The ability to continuously flow samples through a channel has great potential for high throughput microfluidic flow cytometry.

Figure 5:
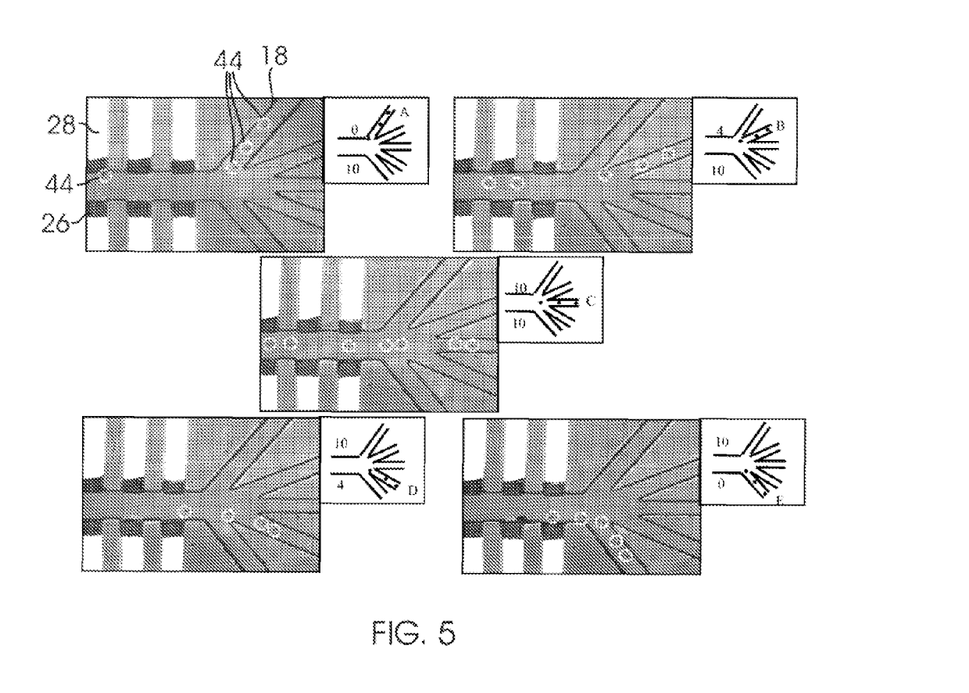
FIG. 5 illustrates a panel of images illustrating a device of the type shown in FIG. 4 that is able to spatially tune the equilibrium position within the microchannel to selectively switch particles (or cells) into one of five (5) downstream branch channels.

FIG. 5 illustrates a panel of images illustrating a device 10 of the type shown in FIG. 4 that is able to spatially tune the equilibrium position within the microchannel 14 to selectively switch particles 44 into one of five (5) downstream branch channels 18. Experiments were conducted using polystyrene microbeads 44 that were introduced into a microchannel 14 having four DEP electrodes 26 on opposing side walls of the microchannel 14. The downstream portion of the microchannel 14 terminated in five (5) branch channels 18.

The carrier fluid for the polystyrene microbeads 44 was an isotonic medium (8.5% sucrose (w/v), 0.3% dextrose (w/v)) dissolved in double deionized water (DDI). The conductivity was adjusted to 0.1 mS/cm with 1640 RPMI used as the DEP buffer solution (using ThermoOrion conductivity/pH meter). The polystyrene microbeads 44 were 6 micron microbeads obtained from a flow cytometry calibration kit (Cat #F13838) (available from Molecular Probe, Inc. of Oregon) and were diluted into the buffer solution after sonication. The solution was then introduced into the microchannel 14 with a controlled flow rate by a PicoPlus (Harvard Apparatus, MA) syringe pump. A dual-channel function generator (Tektronix AFG320) was used to input two separate signals to the two arrays of electrodes 26 (voltage and frequency). The trajectory of the particle motion was recorded using a CCD camera (Photron FASTCAM). The panel of images along with a corresponding graphic representation is shown in FIG. 5. The microbeads 44 appeared to have negative DEP properties in the selected medium with different applied frequencies.

Still referring to FIG. 5, the microbeads 44 were focused or tuned to a variety of spatial locations within the microchannel 14. The tuning was accomplished by changing the either the voltage or the applied frequency on the electrodes 26. As seen in FIG. 5, there are five (5) outlet channels 18. Since the K factor for the microbeads 44 is almost constant at the selected medium conductivity with respect to frequency, switching by voltage difference applied on the two sets of opposing, vertically oriented electrodes 26 was demonstrated. When the microbeads 44 are flowing in the microchannel 14, their trajectory can be adjusted to be away from the centerline of flow (e.g., streamline). As seen in FIG. 5, switching can be extended to channels with multiple outlets. DEP switching thus redirects the objects from the stream line and aligns them towards different outlets or branch channels 18. The top and bottom electrode arrays are applied with same frequency but different amplitudes of voltage to generate different DEP forces. Because the microbeads 44 experienced a negative DEP force, the force from the electrodes 26 with the higher voltage amplitude will be stronger and therefore will deflect the microbeads 44 towards the opposing electrodes 26 driven at the lower amplitude. The equilibrium point(s) 42 for the microbeads 44 can be tuned to any spatial location the width of the microchannel 14. Because of this it is relatively straight forward to expand the switching to multiple outlets or branches 18. While FIG. 5 shows the switching of microbeads 44 into five (5) outlets or branch channels 18 this number could be increased or decreased as needed. In this experiment the microbeads 44 were switched to five different outlet channels sequentially.

As seen in the upper left image of FIG. 5, a voltage of 0 was applied to the top DEP electrodes 26 while a voltage of 10 was applied to the bottom electrodes 26. This caused the microbeads to pass into branch channel A. In the upper right image of FIG. 5, a voltage of 4 was applied to the top DEP electrodes 26 while a voltage of 10 was applied to the bottom electrodes 26. This caused the microbeads to pass into branch channel B. In the upper middle image of FIG. 5, a voltage of 10 was applied to the top DEP electrodes 26 while a voltage of 10 was applied to the bottom electrodes 26. The DEP forces thus being balanced, this caused the microbeads to pass into branch channel C. In the lower left image of FIG. 5, a voltage of 10 was applied to the top DEP electrodes 26 while a voltage of 4 was applied to the bottom electrodes 26. This caused the microbeads to pass into branch channel D. In the lower right image of FIG. 5, a voltage of 10 was applied to the top DEP electrodes 26 while a voltage of 0 was applied to the bottom electrodes 26. This caused the microbeads to pass into branch channel E.

Figure 6:
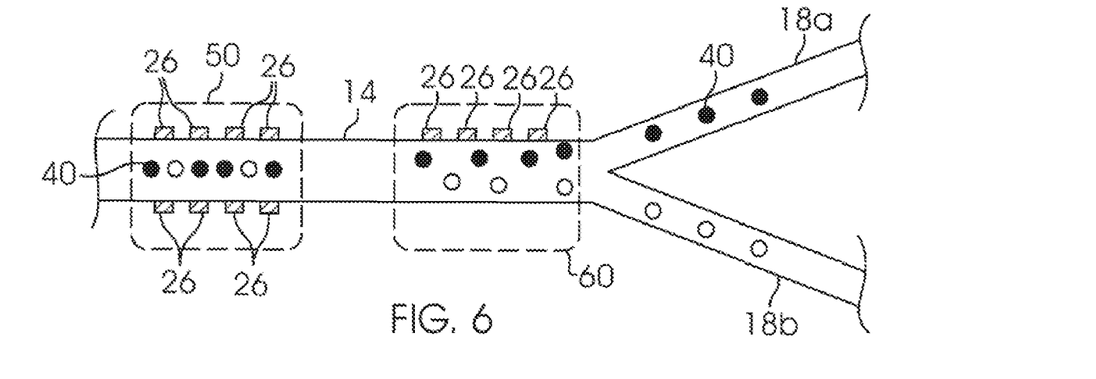
FIG. 6 illustrates one embodiment of a microfluidic device having an upstream focusing region and a downstream separation region.

FIG. 6 illustrates another embodiment of a device 10. In this embodiment, the microchannel 14 includes an upstream focusing region 50 and a downstream separation region 60. The main or common microchannel 14 terminates into a plurality of downstream branches 18 as in the other embodiments described herein. The focusing region 50 is used to focus or align cells 40 or particles 44 to a common, starting location from which separation will occur at a downstream location. In the embodiment of FIG. 6, the focusing region 50 includes opposing arrays of vertically oriented electrodes 26 as described herein. For example, the opposing arrays of electrodes 26 may include DEP electrodes 26 which impart forces in opposing directions on each cell 40 or particle 44. In FIG. 6, two types of cells 40 are aligned or focused in the middle of the microchannel 14 by opposing pairs of DEP electrodes 26.

Once the cells 40 are aligned at a starting location, the cells 40 progress downstream to a separation region 60. In the embodiment of FIG. 6, the separation region comprises an array of vertically oriented DEP electrodes 26 positioned on one side wall of the microchannel 14. Because each cell 40 experiences a different DEP force from the activated electrodes 26 in the separation region 60 the particles become spatially separated in the lateral (i.e., width) direction. As seen in FIG. 6, the solid cells 40 experience very little DEP force and, as a result, fluid flow carries these cells 40 into the upper branch channel 18a. In contrast, the other type of cells 40 (represented by open circles) experiences a larger repulsive force from the active DEP electrodes 26 in the separation region 60. Because of this, these cells 40 are pushed toward the opposing side wall which, in this embodiment, does not have any electrodes 26. The flow of fluid then carries these cells 40 into the lower branch channel 18b.

FIG. 7 illustrates another alternative embodiment of a device 10 using both a focusing region 50 and a downstream separation region 60. In this embodiment, however, a plurality of MHD electrodes 52 are located on a bottom surface of the microchannel 14. The MHD electrodes 52 are generally oriented transverse to the direction of flow within the microchannel 14. The MHD electrodes 52, when driven by a voltage source (not shown), produces a force on the carrying fluid in the direction of arrow A. This causes the cells 40 (or particles 44) to move toward one side of the microchannel 14 as is illustrated in FIG. 7. Here, the cells 40 are all aligned or focused along the wall. The cells 40 then continue downstream to the separation region 60 where, like the prior embodiment of FIG. 6, the cells 40 represented by the solid circles are preferentially moved (in this case attracted) toward the DEP electrodes 26. This causes the solid cells 40 to enter the upper branch channel 18a while the cells 40 represented by the open circles enter the lower branch channel 18b.

As an alternative to the use of MHD electrodes 52 to align or focus cells 40 or particles 44, laminar flow may be used to set the cells 40 or particles 44 in a uniform "start" condition. For example, laminar flow may be used to provide a line of cells 40 or particles 44 along either wall of the microchannel 14. Alternatively, sheath type flow may be used to confine the cells 40 or particles 44 within a centrally located region of the microchannel 14.

Figure 8:
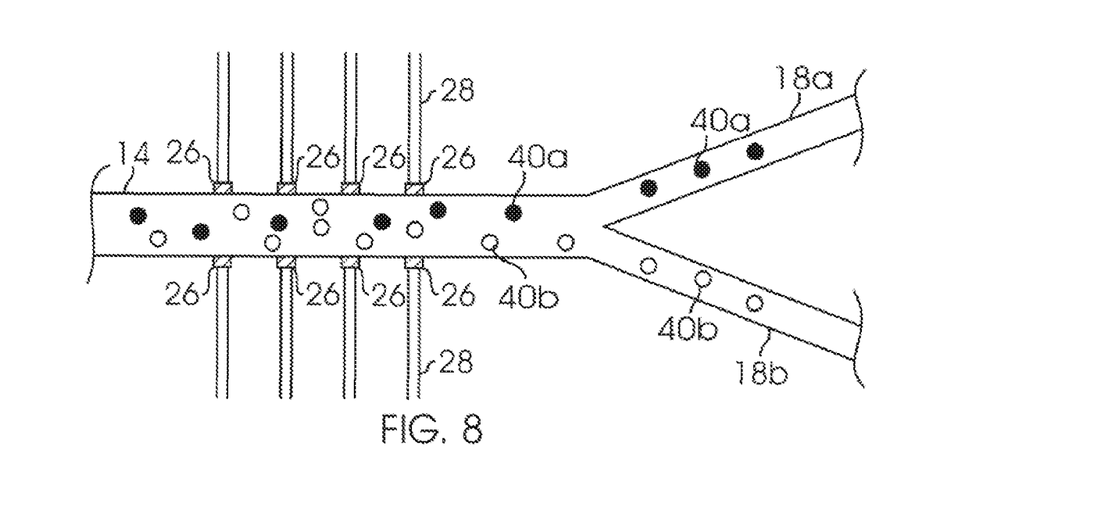
FIG. 8 illustrates a microfluidic device in a free flow configuration. The device illustrated uses opposing arrays of vertically oriented DEP electrodes to separate particles or cells.

FIG. 8 illustrates yet another embodiment of a device 10 that uses vertically oriented electrodes 26 to separate a heterogeneous population of cells 40 or particles 44. The device in FIG. 8 operates in a "free flow" mode. In this regard, unlike the embodiments of FIGS. 6 and 7, the population of cells 40 or particles 44 is not focused or aligned prior to separation. Instead the electrodes 26, which may be DEP electrodes, are driven at different states to spatially separate the cells 40 or particles 44 that flow through the region of the microchannel 14 that contains the opposing set of electrodes 26. For example, the DEP electrodes 26 on one side of the microchannel 14 may be driven at a first frequency while the DEP electrodes 26 on the opposite side of the microchannel 14 are driven at a second, different frequency. By driving the DEP electrodes 26 at different frequencies, the different cells 40 or particles 44 can be spatially separated within the microchannel 40. The voltage amplitudes may also be altered to effectuate spatial separation. In effect, each particular cell type or particle type has a unique "DEP spectra" which can be used to separate a heterogeneous population.

In the device 10 of FIG. 8, the cells of a first type 40a preferentially move toward one side of the microchannel 14 while cells of another type 40b preferentially move toward the other side of the microchannel 14. As the cells move between the electrodes 26 they begin to stratify along the width of the microchannel 14. This spatial separation then causes the two cell types 40a, 40b to flow into different branch channels 18a, 18b. While the embodiment shown in FIG. 8 uses two cell types with two downstream channels, it should be understood that the "free flow" embodiment may be used within populations of cells 40 or particles 44 with more than two types. In this embodiment, the degree of separation is a function of the fluid flow rate as well as the length of the section containing the opposing DEP electrodes 26. A slower flow rate will generally produce greater separation. In addition, more separation may be obtained by increasing the number of electrodes 26.

Figure 9:
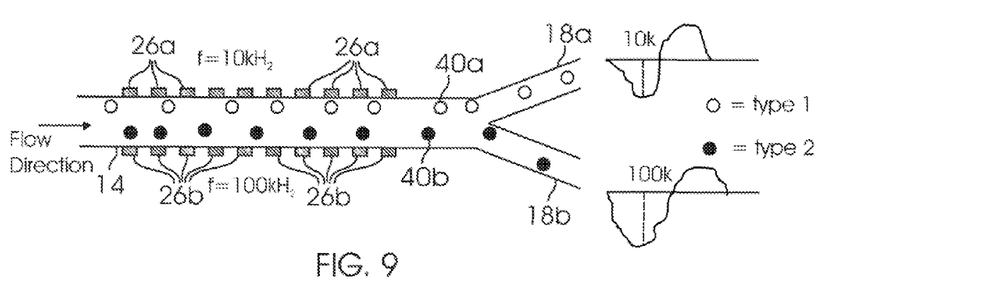
FIG. 9 schematically illustrates operation of a microfluidic device like that shown in FIG. 8.

FIG. 9 graphically illustrates how the device of FIG. 8 operates through the application of different frequencies/amplitudes to the DEP electrodes 26. As seen in FIG. 9, the vertically oriented DEP electrodes 26a on one of the side walls is driven at a frequency of 10 kHz while the opposing vertically oriented DEP electrodes 26b located on the other, opposing side wall is driven at 100 kHz. The voltage (AC) profiles of both sets of electrodes 26a, 26b are also illustrated. As seen in FIG. 9, by driving the DEP electrodes 26a, 26b differently, cells 40a of a first type (e.g., cancer cells) are separated and later sorted into branch channel 18a while cells 40b of a second type (e.g., non cancerous cells) are separated and later sorted into the branch channel 18b.

Figure 10A:
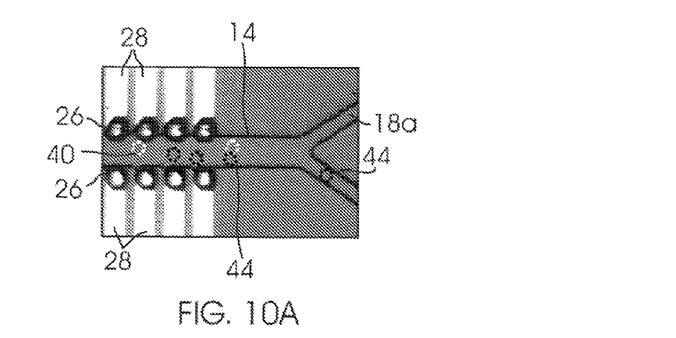
FIGS. 10A and 10B illustrate photographic images of cells and microbeads being separated in a microfluidic device like those illustrated in FIGS. 8 and 9.
Figure 10B:
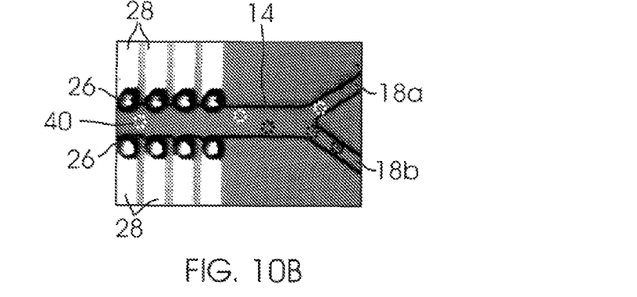

A DEP-DEP "free flow" device like that shown in FIGS. 8 and 9 was tested for its ability to separate and sort cells 40 from microbeads 44. A device 10 having opposing DEP electrodes 26 was used to separate polystyrene microbeads 44 and HEK 293 cells 40. Separation was accomplished by using different driving frequencies for the opposing arrays of DEP electrodes 26. Both cells 40 and microbeads 44 were introduced into the microchannel 14 at the same time. The cells 40 as shown in FIGS. 10A and 10B (shown circled by white colored dots) preferentially moved toward the upper DEP electrodes 26 while the microbeads 44 (shown circled by darkened dots) experienced attraction toward the lower set of DEP electrodes 26. The cells 40 were then sorted into the upper branch channel 18a while the particles 44 were then sorted into the lower branch channel 18b.

Figures 11A, 11B, 12A:
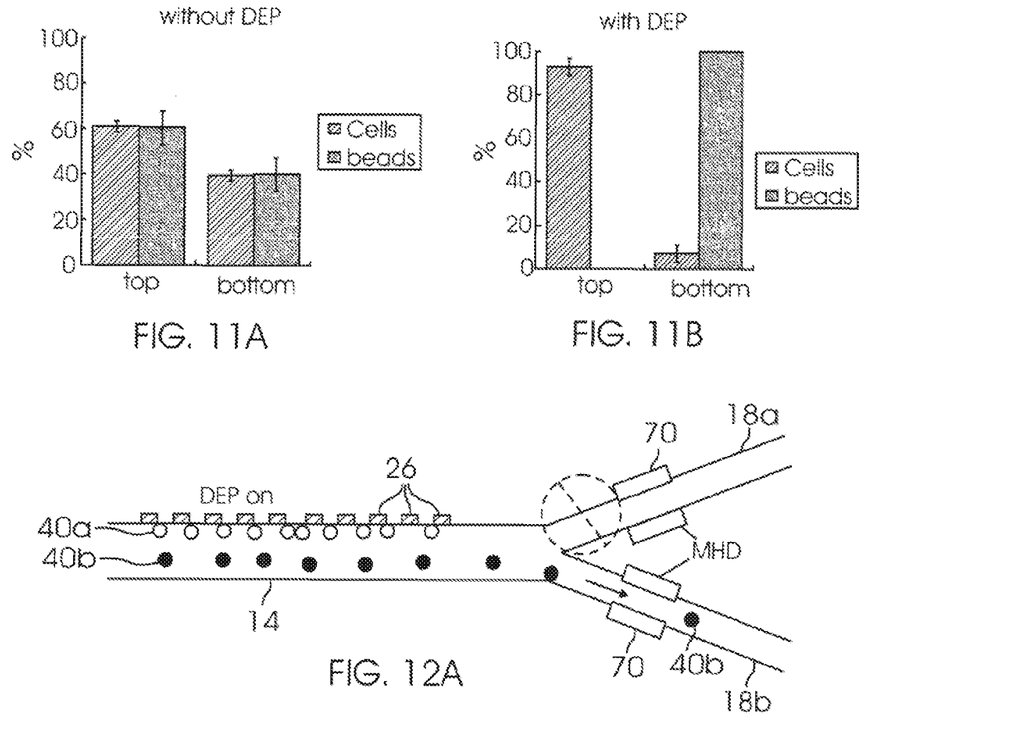
FIGS. 11A and 11B illustrate graphs showing collection percentage for cells and microbeads with the electrodes in an off state (FIG. 11A) and on state (FIG. 11B).
FIGS. 12A and 12B illustrate another embodiment of a microfluidic device that traps certain cells or particles of a heterogeneous population using DEP electrodes for subsequent separation and sorting.

FIG. 11A illustrates the sorting percentage of the device 10 without the DEP electrodes 26 being powered. As seen in FIG. 11A, the cells 40 and microbeads 44 were nearly equally distributed in the top and bottom branch channels 18a, 18b. In contrast, as seen in 11B, when the DEP electrodes 26 were activated, the cells 40 were separated and sorted into the top branch channel 18a while the microbeads 44 were separated and sorted into the bottom branch channel 18b. This sorting device 10 and method is thus able to simultaneously discriminate and sort a heterogeneous population of cells 40 and particles 44. This is important because the device 10 may have relatively high throughput levels.

Figure 12B:
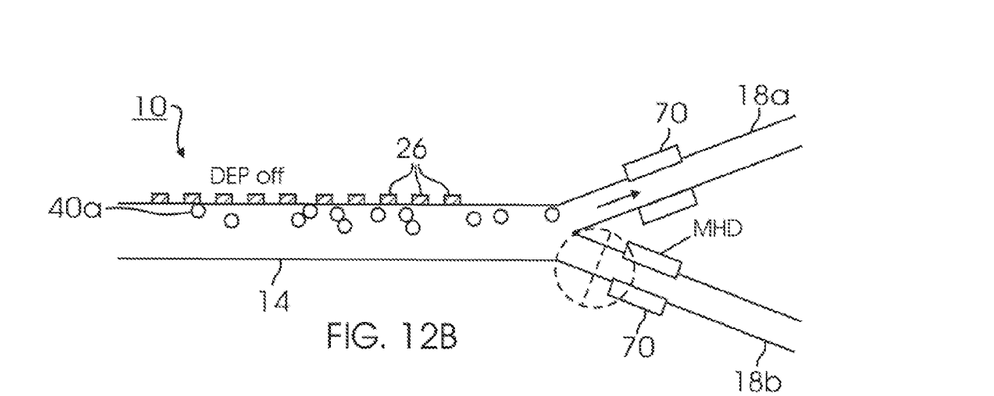

FIGS. 12A and 12B illustrate an embodiment of a device 10 that uses DEP electrodes 26 to effectuate separation and sorting of cells 40 or particles 44 by trapping. In this device 10, DEP electrodes 26 are positioned on one side of the microchannel 14. The DEP electrodes 26 are driven such that cells 40 or particles 44 are temporarily trapped along the side wall of the microchannel 14. For example, as shown in FIG. 12A, cells 40a are trapped when the DEP electrodes 26 are energized while the cells 40b are not trapped and flow downstream in the fluid flow. The device 10 may include multiple branch channels 18a, 18b with each associated with a MHD valve 70. The MHD valves 70 can be turned on or off to shunt fluid flow to a particular branch channel 18. For example, in FIG. 12A, the upper branch channel 18a is closed to permit the cells 40b to sort into the lower branch channel 18b. Once the cells 40b have entered the branch channel 18b, the MHD valve 70 associated with branch channel 18b is closed and the MHD valve for branch channel 18a is opened (as shown in FIG. 12B). The trapped cells 40a can then be released by de-energizing the DEP electrodes 26. The cells 40a are then free to flow into the other branch channel 18a.

Figure 13A:
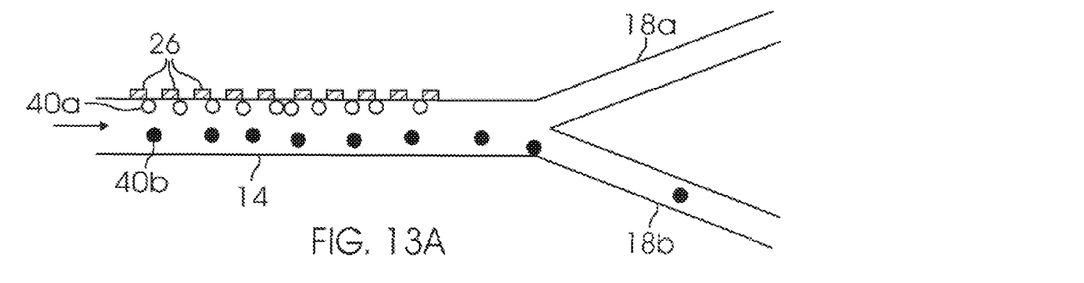
FIGS. 13A and 13B illustrate another embodiment of a microfluidic device that traps certain cells or particles of a heterogeneous population for subsequent separation and sorting.
Figure 13B:
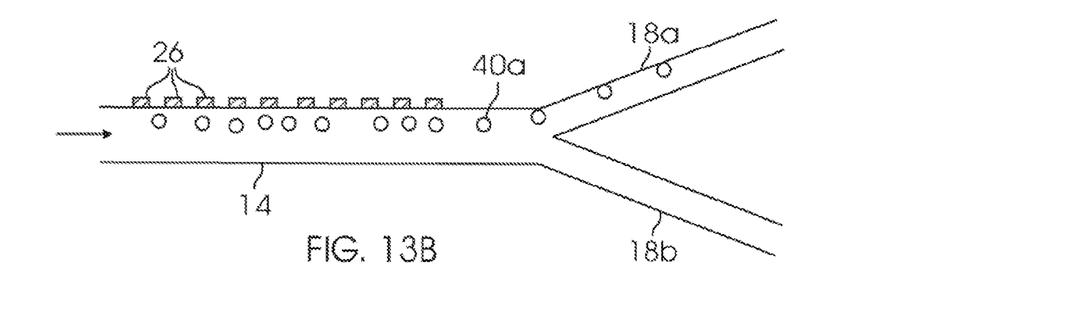

The trapping aspect may also be integrated into "free flow" embodiments described herein. FIGS. 13A and 13B illustrate a device 10 and method that traps cells 40 or particles 44 in a free flow setting. In this embodiment, DEP electrodes 26 are positioned along one side wall of the microchannel 14. The DEP electrodes 26 are capable of being driven so as to trap certain cells 40 or particles 44 passing through the microchannel 14. Mixed populations of cells 40 (or particles 44) are pumped into the microchannel 14. When the DEP electrodes 26 are turned on as shown in FIG. 13A, cells types 40a are trapped to the DEP electrodes 26. Meanwhile the other type of cells 40b are repelled from the electrodes 26 and flow out the branch channel 18b. The trapped cells 40a are then released by turning off the DEP electrodes 26. The cells 40a then naturally flow into the branch channel 18a. In this embodiment, there is no need for downstream valves or the like to aid in sorting the trapped cells 40.

In addition, in another embodiment, the portion of the microchannel 14 that is downstream of the trapping DEP electrodes 26 may include a plurality of electrodes 26 that are used to selectively switch cells 40 or particles 44 into one or more selected branch channels 18. In this regard, downstream electrodes 26 may be used to actively separate cells 40 or particles 44 into the appropriate branch channel 18. For example, in this embodiment a cluster or group of cells 40 of a given type may be trapped while a cluster or group of cells 40 of another type are eluted passed the trapping DEP electrodes 26. The eluted cells 40 may be actively moved into a particular branch channel 18 via a plurality of downstream-located electrodes 26. The "trapped" cells 40 of the first type may then be released into the fluid flow. These formerly trapped cells 40 can then be actively guided via charged electrodes 26 into another branch channel 18 via the downstream-located electrodes 26.

Figure 14A:
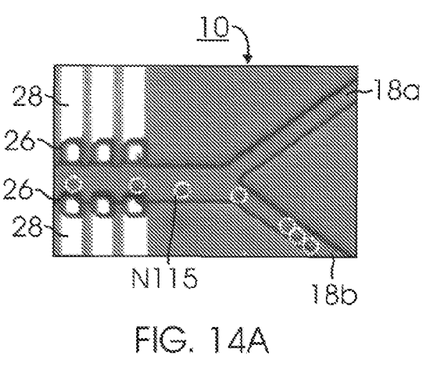
FIGS. 14A and 14B illustrate photographic images of a trapping microfluidic device that is used to separate and sort N115 cells from HEK293 cells.
Figure 14B:
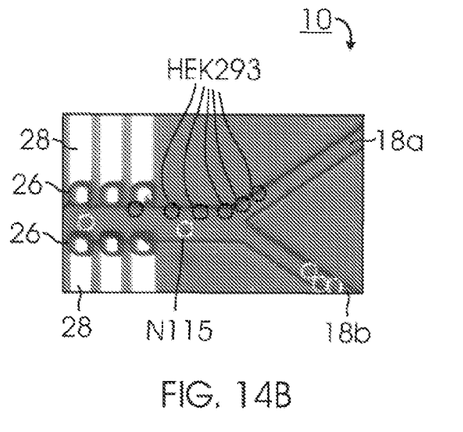

FIGS. 14A and 14B illustrate photographic images of a trapping device 10 like that illustrated in FIGS. 13A and 13B being used to trap and sort HEK293 cells 40 from N115 cells 40. In FIG. 14A, HEK293 cells are trapped on the DEP electrodes 26 (in FIG. 14A the trapping is upstream and out of view of the image) while the N115 cells (circled by white colored dots) are repelled away from the DEP electrodes 26 and flow into the bottom branch channel 18b. FIG. 14B illustrates the DEP electrodes 26 being turned off with the HEK293 cells (circled by black colored dots) were released from the DEP electrodes 26 and flow into the top branch channel 18a.

While embodiments of the present invention have been shown and described, various modifications may be made without departing from the scope of the present invention. The invention, therefore, should not be limited, except to the following claims, and their equivalents.

What is claimed is:

1. A microfluidic separation device comprising:
 a first microchannel formed in a substrate, the first microchannel being defined by a bottom surface, a first wall, and second wall, the first microchannel including an upstream end and a downstream end;
 a plurality of magneto-hydro dynamic electrodes disposed on the first wall configured to apply a substantially uniform force oriented generally perpendicular to a long axis of the first microchannel;
 a plurality of dielectrophoretic electrodes disposed on the second wall opposite to the first wall configured to apply a substantially non-uniform force oriented generally perpendicular to a long axis of the first microchannel and opposite the force of the plurality of magneto-hydro dynamic electrodes;
 a voltage source connected to the plurality of electrodes on the first wall and the second wall; and
 a plurality of branch microchannels coupled to a downstream end of the first microchannel.

2. The device of claim 1, wherein the first microchannel is configured to connect to a source of heterogeneous cells.

3. The device of claim 1, wherein the first microchannel is configured to connect to a source of heterogeneous particles.

4. The device of claim 1, further comprising a plurality of electrodes disposed on one of the first wall or the second wall at a position that is downstream of the opposing plurality of electrodes and upstream of the branch channels.

5. The device of claim 4, wherein the plurality of electrodes disposed on one of the first wall or the second wall at a position that is downstream of the opposing plurality of electrodes and upstream of the branch channels is connected to a separate voltage source.

6. The device of claim 1, further comprising a top surface covering the microchannel.

7. The device of claim 1, wherein the plurality of branch channels include two or more branch channels.

8. A microfluidic separation device comprising:
 a first microchannel formed in a substrate, the first microchannel being defined by a bottom surface, a first wall, and second wall, the first microchannel including an upstream end and a downstream end;
 a focusing region disposed in the first microchannel comprising a plurality of electrodes disposed on the first wall and another plurality of electrodes disposed on the second wall opposite the plurality of electrodes disposed on the first wall;
 a voltage source connected to the plurality of electrodes on the first wall and the second wall;
 a separation region disposed in the first microchannel at a location downstream of the focusing region, the separation region comprising a plurality of magneto-hydro dynamic electrodes disposed on a first wall of the first microchannel and configured to apply a substantially uniform force oriented generally perpendicular to a long axis of the first microchannel and a plurality of dielectrophoretic electrodes disposed on a second wall of the first microchannel and configured to apply a substantially non-uniform force oriented generally perpendicular to a long axis of the first microchannel and opposite the force of the plurality of magneto-hydro dynamic electrodes of the first microchannel; and
 a plurality of branch microchannels coupled to a downstream end of the first microchannel.

9. The device of claim 8, wherein the first microchannel is configured to connect to a source of heterogeneous cells.

10. The device of claim 8, wherein the first microchannel is configured to connect to a source of heterogeneous particles.

11. The device of claim 8, wherein the plurality of electrodes disposed in the separation region are connected to a separate voltage source.

12. The device of claim 8, further comprising a top surface covering the microchannel.

13. The device of claim 8, wherein the plurality of branch channels include two or more branch channels.

14. A method of sorting particles or cells using a microfluidic device comprising:
 providing a microfluidic channel having a bottom surface and two opposing side walls, the microfluidic channel having a focusing region comprised of a plurality of electrodes disposed on opposing side walls of the microchannel, the microfluidic channel further including a separation region located downstream of the focusing region and comprising a plurality of magneto-hydro dynamic electrodes disposed on one side of the side wall and a plurality of dielectrophoretic electrodes disposed on an opposing side of the side wall, the microchannel further including a plurality of branch channels located downstream of the separation region;
 flowing a heterogeneous population of particles or cells within the microfluidic channel;
 driving the plurality of electrodes in the focusing region to align the heterogeneous population of particles or cells within the microchannel;
 driving the magneto-hydro dynamic electrodes to urge the heterogenous population of particles or cells toward the opposing dielectrophoretic electrodes;
 driving the plurality of dielectrophoretic electrodes in the separation region so as to spatially separate the heterogeneous population of particles or cells; and
 flowing the spatially separate heterogeneous population of particles or cells into the plurality of branch channels based at least in part on the spatial separation.

15. A method of sorting particles or cells using a microfluidic device comprising:
 providing a microfluidic channel having a bottom surface and two opposing side walls, the microfluidic channel having a plurality of magneto-hydro dynamic electrodes disposed on one side of the microfluidic channel and a plurality of dielectrophoretic electrodes disposed on an opposing side of the microfluidic channel, the microfluidic channel further including a plurality of branch channels located downstream of the plurality of electrodes;
 flowing a heterogeneous population of particles or cells within the microfluidic channel;
 driving the magneto-hydro dynamic electrodes to urge the heterogenous population of particles or cells toward the opposing dielectrophoretic electrodes;
 driving the plurality of dielectrophoretic electrodes so as to spatially separate the heterogeneous population of particles or cells; and
 flowing the spatially separate heterogeneous population of particles or cells into the plurality of branch channels based at least in part on the spatial separation.

* * * * *